United States Patent
Pang et al.

(10) Patent No.: US 7,358,342 B2
(45) Date of Patent: Apr. 15, 2008

(54) PREPARATION DERIVED FROM SHARK CARTILAGE FOR TREATMENT OF DISEASED RELATED TO EXCESSIVE PHF OR EXCESSIVE INTRACELLULAR CALCIUM

(75) Inventors: Peter K. T. Pang, Edmonton (CA); Jacqueline J. Shan, Edmonton (CA); Kam Chiu, Edmonton (CA)

(73) Assignee: fX Life Sciences International GmbH, Zug (CH)

( * ) Notice: Subject to any disclaimer, the term of this patent is extended or adjusted under 35 U.S.C. 154(b) by 96 days.

(21) Appl. No.: 10/825,661

(22) Filed: Apr. 16, 2004

(65) Prior Publication Data

US 2004/0234617 A1 Nov. 25, 2004

Related U.S. Application Data

(63) Continuation of application No. 09/462,094, filed as application No. PCT/US98/13591 on Jul. 9, 1998, now abandoned.

(60) Provisional application No. 60/052,233, filed on Jul. 11, 1997.

(51) Int. Cl.
*C07K 1/14* (2006.01)
*A61K 38/00* (2006.01)

(52) U.S. Cl. .................... 530/422; 530/350; 530/412; 530/427; 514/21

(58) Field of Classification Search ................ 530/412, 530/422; 514/21
See application file for complete search history.

(56) References Cited

U.S. PATENT DOCUMENTS

| | | | | |
|---|---|---|---|---|
| 3,371,012 A | * | 2/1968 | Furuhashi | |
| 4,473,551 A | * | 9/1984 | Schinitski | 424/95 |
| 5,512,591 A | * | 4/1996 | Halperin et al. | 514/399 |
| 5,618,925 A | * | 4/1997 | Dupont et al. | 530/400 |
| 5,985,839 A | * | 11/1999 | Dupont et al. | 514/21 |
| 6,025,334 A | * | 2/2000 | Dupont et al. | 514/21 |
| 6,028,118 A | * | 2/2000 | Dupont et al. | 514/863 |

FOREIGN PATENT DOCUMENTS

WO 97/16197 A1 5/1997

OTHER PUBLICATIONS

Echard et al. Database Medline, DN 21572448, Mol. Cell. Biochem., 2001, vol. 225, 85-91.*
J. Paediatr. Child Health, 1996, vol. 32, pp. 419-423, Tang and Miller (Abstract only).

* cited by examiner

*Primary Examiner*—Michael Borin
(74) *Attorney, Agent, or Firm*—Rothwell, Figg, Ernst & Manbeck, P.C.

(57) ABSTRACT

A preparation derived from shark cartilage for the treatment of diseases related to excessive PHF or Excessive intracellular calcium.

4 Claims, 8 Drawing Sheets

PREPARATION DERIVED FROM SHARK CARTILAGE FOR TREATMENT OF DISEASED RELATED TO EXCESSIVE PHF OR EXCESSIVE INTRACELLULAR CALCIUM

CROSS REFERENCE TO RELATED APPLICATION

This application is a continuation of application Ser. No. 09/462,094 filed on Jan. 11, 2000 now abandoned, which is a 35 USC §371 national phase entry application of PCT/US98/13591 filed on Jul. 9, 1998 designating the U.S., which claims priority from U.S. provisional application No. 60/052,233 filed on Jul. 11, 1997.

FIELD OF THE INVENTION

This invention relates to an anti-parathyroid hypertensive factor (anti-PHF) derived from shark cartilage. The compounds of the present invention can be used in the treatment of hypertension, and other diseases related to intracellular calcium elevation (e.g., non-insulin dependent diabetes mellitus; atherosclerosis; congestive heart failure; cancer (including breast, colon, kidney and leukemia); inflammatory bowel disease and asthma.

BACKGROUND OF THE INVENTION

Hypertension is generally defined as the elevation of the systolic and/or diastolic arterial blood pressure above a nominal value of 140/90 mm Hg. Diseases associated with hypertension include arteriosclerosis, hypertensive renal failure, stroke, congestive heart failure and myocardial infarction. Although numerous methods of treatment have been found to be effective in the reduction of arterial blood pressure, the etiology of essential hypertension remains essentially unknown. A genetic predisposition to hypertension is generally accepted, but the number of different drugs which have been found effective in the treatment of hypertension, and the fact that these drugs seem to operate by eliciting different pharmacological responses, suggests that there may be different primary causes for essential hypertension.

A number of studies have suggested that one or more circulating factors may play a role in the genesis or the maintenance of hypertension [See: Wright et al., A Hypertensive Substance Found in the Blood of Spontaneously Hypertensive Rats; *Life Sci.* 1984; 34:1521-1528; Dahl et al., Humoral transmission of Hypertension: Evidence from Parabiosis; *Circ. Res.* 1969; 24/25 (Supp. I): 21-23; Greenberg et al., Evidence for Circulating Factors as a Cause of Venous Hypertrophy in Spontaneously Hypertensive Rats; *Am. J. Physiol.* 1981; 241:H421-H430; Tobian et al., A Circulating Humoral Pressor Agent in Dahl S Rats with Salt Hypertension; *Clin. Sci.* 1979; 57:345s-347s; Zidek et al., Humoral Factors in the Pathogenesis of Primary Hypertension: *Klin. Wochenschr.* 1985; 63 (Supp. II) D:94-96; Hirata et al., Hypertension Producing Factor in the Serum of Hypertensive Dahl Salt-Sensitive Rats; *Hypertension* 1984; 6:709-716]. For example, in parabiosis and cross-circulation experiments, an increase in blood pressure could be induced in normotensive animals by exposure to blood from hypertensive animals. The subcutaneous injection of erythrocyte-associated factor obtained from spontaneously hypertensive rates (SHR) has been shown to induce hypertension in normotensive Wistar-Kyoto (WKY) rats and an increase in blood pressure can be induced in normotensive, salt insensitive Dahl rats by injection of serum from hypertensive, salt-sensitive Dahl rats.

There have also been reports of circulating factors in both hypertensive rats and hypertensive humans which increase intracellular calcium. [See: Banos et al., Two Factors Associated with Increased Uptake of Calcium in Platelets from Essential Hypertensive Patients; *Clin. Exp. Hypertens.* 1987; 9:1515-153; Zidek et al., Effect of Plasma from Hypertensive Subjects on Ca Transport in Permeabilized Human Neutrophils; *Clin. Sci.* 1988; 74:53-56; Linder et al., Effects of a Circulating Factor in Patients with Essential Hypertension on intracellular Free Calcium in Normal Platelets; *N. Eng. J. Med.* 1987; 316:509-513; Bruschi et al., Cytoplasmic Free Ca is Increased in the Platelets of Spontaneously Hypertensive Rats and Essential Hypertensive Patients; *Clin. Sci.* 1985; 68:179-184; Wright et al., Stimulation of Aortic Tissue Calcium Uptake by an Extract of Spontaneously Hypertensive Rat erythrocytes Possessing Hypertensive Properties; *Can. J. Physiol. Pharmacol.* 1986; 64:1515-1520]. Since vascular tone is influenced by the level of intracellular calcium, factors which increase blood pressure and factors which increase intracellular calcium may be related. There has been accumulating evidence suggesting the involvement of calcium regulating hormones in some forms of hypertension [See: L. M. Resnick, *Am. J. Med.* 82 (Supp. 1B), 16 (1987)]. Parathyroid hormone (PTH) is a calcium regulating hormone. Thirty percent or more of essential hypertensive patients fall into a subgroup characterized by increased levels of immunoreactive parathyroid hormone (ir-PTH). [See: Laragh et al., *Kidney Int.* 34, (Supp. 35), S162 (1988)]. An increase in PTH levels has been reported in SHR rats [See: McCarron et al., *Hypertension* 3 (Supp. 1), I162 (1981)] and it has been observed that hyperparathyroid patients often exhibit hypertension, the severity of which can, in most cases, be reduced by parathyroidectomy [See: Hellstrom et al., *Brit. J. Urol.* 30, 13 (1958)]. Similar results from parathyroidectomy have also been reported in SHR rats. [See: Schleiffer et al., *Jap. Circ. J.* 45, 1272 (1981)]. Various investigators have suggested that PTH contributes to the development of essential hypertension, although exogenous administration of PTH causes a reduction in blood pressure in mammals and other vertebrates [See: Pang et al., *Gen. Comp. Endocrinol.* 41, 135 (1980)]. The vasodilating action of PTH is also related to a specific region of the molecule separate from the region mediating hypercalcemic effects [See: Pang et al., *Endocrinology*, 112, 284 (1983)]. PTH has also been shown to inhibit calcium entry into vascular smooth muscle [See: Pang et al., *Life Sci.*, 42, 1395 (1988)] through L-type calcium channels [Wang et al. FEBS, Vol. 282, No. 2, pp. 331-334 (1991)]. This paradox is further heightened by the fact that hypertensive patients with increased PTH levels exhibit decreased serum ionized calcium levels [See: Resnick et al., *New Engl. J. Med.*, 309, 888 (1983); Hvarfner et al., *Acta Med. Scand.* 219, 461 (1986)]. It would be expected that the serum ionized calcium levels would be elevated if PTH were primarily elevated.

The existence of a circulating factor in the blood of the SHR rat was confirmed by the studies reported in *Am. J. Hypertens.*, 2, 26-31 (1989). In these studies, an increase in the blood pressure of WKY and SD rats when plasma from SHR rats was injected into the normotensive rats either by infusion or by bolus injection was shown. In addition, it has been shown that the uptake of $^{45}Ca$ by sections of the tail artery of a rat, in vitro, increased in a dose-dependent manner as the concentration of SHR plasma was increased in a buffer-based medium. The results of these experiments clearly show that an increase in blood pressure and an increase in calcium uptake in the cells were both dose-dependent on the amount of SHR plasma present and available in the system. Curiously, the onset of both events was delayed, and gradual, whereas known endogenous pressor agents such as norepinephrine, angiotensin II and vasopressin have been observed to increase blood pressure quite rapidly after administration. The known endogenous pressor agents exhibit about a 1-2 minute onset in the increase of blood pressure and increase in calcium uptake in the cells whereas parathyroid hypertensive factor has a 20-30 minute delay before such onset. Another result observed in these studies was that when the infusion of SHR plasma was stopped and substituted with plasma from normotensive rats, the observed blood pressure decreased quite rapidly to the baseline. The decrease observed precluded a simple volume effect. In a related experiment, dialyzed plasma from hypertensive human subjects was infused into normotensive SD rats and shown to produce hypertension. Plasma from these subjects also increased calcium uptake in rat tail arteries in vitro. Dialyzed plasma from normotensive patients produced no significant increase in blood pressure.

The origin of the circulating factor was unknown, but the anecdotal reports that PTH was elevated in hypertensive rats suggested the parathyroid gland as a target of investigation. Parathyroidectomies of SHR rats were found to reduce blood pressure and plasma from the SHR rats which had been parathyroidectomized did not cause elevation of blood pressure in normotensive rats. Conversely, transplantation of parathyroid glands from SHR rats to normotensive Sprague-Dawley (SD) rats resulted in an increase in blood pressure and the appearance of the factor in the plasma, as shown by infusion of the isolated plasma into other normotensive rats. [Pang and Lewanczuk, Amer. J. Hypertens. 2, 898 (1989)].

On the basis of these studies, the parathyroid was determined to be the origin of the circulating factor and the name "Parathyroid Hypertensive Factor" or PHF was proposed for the substance which causes an elevation in blood pressure.

The isolation and purification of a circulating factor, having its origin in the parathyroid gland, has been demonstrated in SHR rats and in many humans having essential hypertension and is the subject matter of related patent application Ser. No. 603,745 filed Nov. 21, 1990, which is a continuation-in-part of patent application Ser. No. 327,450, filed Mar. 22, 1989, now abandoned. The disclosure of the related patent applications are incorporated herein by reference for their teachings, including the teachings of purification of parathyroid hypertensive factor.

As described in the aforementioned related patent applications, PHF has been shown to regulate extracellular calcium uptake, and can be inhibited by increases in dietary calcium levels. PHF has been isolated and a method for screening for PHF using antibodies raised against PHF have been described. PHF has a molecular weight of approximately 2,700 daltons and has the property of delayed onset of an increase in blood pressure of a normotensive rat when administered thereto, the increase in blood pressure temporally correlating with an increase in extracellular calcium uptake by vascular smooth muscle. From bioassay data, the factor in humans and rats has been found to be substantially similar.

Vascular hypertrophy has been implicated in the pathophysiology of a number of cardiovascular diseases including essential hypertension. Vascular smooth muscle proliferation could account for vascular hypertrophy and increased vascular tone. It was reported that PHF increased vascular smooth muscle cell proliferation through a mechanism independent of intracellular calcium regulation (Shan et al., Abstract in 17th Scientific Meetings of the International Society of Hypertension, Amsterdam, 7-11 Jun. 1998).

Antagonists of PHF have been found by the present inventors. The present inventors have unexpectedly found that shark cartilage, known in the art to contain a substance which inhibits tumor angiogenesis [Lee et al., Science, vol. 221, pp.1185-1187, (1983)] and to contain an anti-inflammatory component [Schinitsky U.S. Pat. No. 4,473,551], acts as an antagonist of PHF resulting in a decrease in blood pressure and affecting intracellular calcium regulation. The present inventors have also found that shark cartilage extract inhibited VSMC proliferation in SHR rats or in WKY rats induced by PHF. In view of this, shark cartilage extract according to the present invention is expected to be useful for treating hypertension and other diseases related to intracellular calcium elevation.

DETAILED DESCRIPTION OF THE INVENTION

The present inventors have found that an extract prepared from shark cartilage produces a decrease in blood pressure. The shark cartilage extract is believed to contain a parathyroid hypertensive factor antagonist which binds to the parathyroid hypertensive factor site without activating parathyroid hypertensive factor activity.

The shark cartilage extract can be obtained by further purifying commercially available shark cartilage which has been cleaned, dried and milled to a fine powder. The dried-ground shark cartilage is first extracted with $H_2O$ at a temperature between 4-120° C. (preferably 95° C.) for 2-4 hours (preferably 2 hours). The ratio of solute to solvent is between 1:8 and 1:12. The resulting suspension is then cooled to between 40-60° C. (preferably 50° C.) and centrifuged at about 5200 to 5700 rpm to separate the suspension into a supernatant (#1) and pellet. The supernatant (#1), which contains about 8% solids, is held in a cooling tank at 4-8° C. while the pellet is subjected to a second extraction. In the second extraction the pellet is extracted with $H_2O$ at a temperature between 4-120° C. (preferably 95° C.) for 2-4 hours (preferably 2 hours). The ratio of solute to solvent is 1:4-1:6 (based on starting material). The resulting suspension is then cooled to between 40-60° C. (preferably 50° C.) and centrifuged at about 5200 to 5700 rpm to separate the suspension into a supernatant and pellet. The supernatant is then pooled with the supernatant from the first extraction and spray dried to obtain the purified shark cartilage extract of the present invention.

The extract of the present invention may be administered to a warm blooded mammal in need of such treatment, by parenteral, topical, oral or rectal administration or by inhalation. The extract may be formulated for parenteral or oral dosage by compounding the extract with a conventional vehicle, excipient, binder, preservative, stabilizer, color, agent or the like as called for by accepted pharmaceutical practice.

For parenteral administration, a 1-10 ml intravenous, intramuscular or subcutaneous injection would be given one to four times daily. The injection would contain the shark cartilage extract of the present invention in an aqueous isotonic sterile solution or suspension optionally with a preservative such as phenol or a solubilizing agent such a ethylenediaminetetraacetic acid (EDTA). Among the acceptable vehicles and solvents that may be employed are water, Ringer's solution and isotonic sodium chloride solution. In addition, sterile, fixed oils are conventionally employed as a solvent or suspending medium. Synthetic monoglycerides, diglycerides, fatty acids (such as oleic acid) find use as fixed oils in the preparation of injectables.

For rectal administration, the extract can be prepared in the form of suppositories by mixing with a suitable non-irritating excipient such as cocoa butter or polyethylene glycols.

For topical use, the extract can be prepared in the form of ointments, jellies, solutions, suspensions or dermal adhesive patches.

In a powdered aerosol, the extract may be administered by a Spinhaler turbo-inhaler device obtained from Fisons Corporation of Bedford, Mass., at a rate of about 0.1 to 50 mg per capsule, 1 to 8 capsules being administered daily for the average human. In a liquid aerosol, the extract is administered at the rate of about 100 to 1000 micrograms per "puff" or activated release of a standard volume of propellant. The liquid aerosol would be given at the rate of 1 to 8 "puffs" per day with variation in dosages due to the severity of the conditions being treated, the weight of the patient and the particle size distribution of the aerosol. A fluorinated hydrocarbon or isobutane can be used as propellants for liquid aerosols.

Daily doses are in the range of about 0.01 to about 200 mg per kg of body weight (preferably 1-10 mg/kg body weight) depending on the activity of the specific compound, the age, weight, sex and conditions of the subject to be treated, the type and severity of the disease, the frequency and route of administration. As would be well known, the amount of active ingredient that may be combined with the carrier materials to produce a single dosage will vary depending upon the host treated and the particular mode of administration.

The shark cartilage extract can also be combined with drugs known to be effective for treating the condition in question. For example, to treat hypertension, shark cartilage extract can be combined with known antihypertensive drugs such as calcium channel blockers (e.g. verapamil, nifedipine and diltiazem).

In addition to the treatment of essential hypertension, the extract of the present invention can be used to treat other diseases which may include but do not necessarily include hypertension as a primary symptom. For example, noninsulin dependent diabetics are frequently hypertensive. Conversely, hypertensives frequently show an impaired glucose tolerance. Thus, shark cartilage extract is expected to be useful for treating hypertension and other diseases related to intracellular calcium elevation.

The present invention is intended to encompass the isolation, identification and synthetic production of the active ingredient from shark cartilage extract.

The following examples illustrate but are not intended to limit the present invention. Various modifications may be apparent to those skilled in the art without deviating from the scope of this invention.

EXAMPLE 1

Extraction of Shark Cartilage

Cleaned, dried, ground shark cartilage was purchased. The dried ground shark cartilage was first extracted with $H_2O$ at a temperature between 85° to 90° C. for 2 hours. The ratio of solute to solvent was 1:8. The resulting suspension was then cooled to 50° C. and centrifuged at 5200 rpm (3245 g) to separate the suspension into a supernatant and pellet. The supernatant, which contained about 8% solids, was held in a cooling tank at 4° C. while the pellet was subjected to a second extraction. In the second extraction the pellet was extracted with $H_2O$ at 95° C. for 3 hours. The ratio of solute to solvent was 1:4.8 based on the starting material. The resulting suspension was then cooled to 50° C. and centrifuged at 5200 rpm (3245 xg) to separate the suspension into a supernatant and pellet. The supernatant, which contained about 3% solids, was pooled with the supernatant from the first extraction and spray dried to obtain the purified shark cartilage extract of the present invention.

EXAMPLE 2

Effect of Bolus Injection of Shark Cartilage Extract (1 mg/kg) in SHR and SD Rats Six (6) spontaneously hypertensive rats (SHR) and three (3) Sprague-Dawley (SD) rats were given an intravenous bolus injection of shark cartilage extract denoted as DFI-40. Five (5) spontaneously hypertensive rats (SHR) and three (3) Sprague-Dawley (SD) rats were given an intravenous bolus injection of shark cartilage extract denoted as DF II-40. The shark cartilage extract was administered at a dosage of 40 mg/kg body weight. Blood pressure was measured for 90 minutes after the injection. As shown in FIG. 1, the shark cartilage extract produced no effect in SD rats but decreased the blood pressure in SHR rats.

EXAMPLE 3

Effect of Savage Administration of Shark Cartilage Extract on SHR and SD Rats

Three groups of SHR rats were gavage fed with three different doses of shark cartilage extract (10, 20 and 40 mg/kg) from batch DF II-53. 11 rats were administered 10 mg/kg body weight shark cartilage extract, 4 rats were administered 20 mg/kg body weight shark cartilage extract and 4 rats were administered 40 mg/kg body weight shark cartilage extract. Blood pressure was measured for 90 minutes after administration. As shown in FIGS. 2, 2a and 2b, all of the rats showed a decrease in blood pressure which was dose related. In rats given higher doses, (20-40 mg/kg body weight), the rate of decrease in blood pressure is greater with the maximum decrease being reached at around 50-60 minutes (FIG. 2a). After 50-60 minutes, the blood pressure fluctuates possibly due to the blood pressure regulating mechanisms of the rat.

EXAMPLE 4

Effect of PHF on the Blood Pressure of SD Rats in the Presence and Absence of Shark Cartilage Extract Seven (7) SD rats were administered 1 ml equivalent of PHF by IV bolus injection. Six (6) SD rats were administered 1 ml equivalent of PHF by IV bolus injection and 10 minutes later 40 mg/kg body weight of shark cartilage extract (DF II-53) was administered. Blood pressure was measured for 90 minutes following the injections. As shown in FIG. 3, PHF produces a delayed increase in blood pressure and the shark cartilage extract counteracts this response.

EXAMPLE 5

Effect of PHF on Vascular Smooth Muscle Cell (VSMC) Proliferation in the Presence and Absence of Shark Cartilage Extract The tail artery of male West Kyoto (WKY) rats or Spontaneous Hypertensive Rats (SHR) (100-200 g body weight) was dissected out and immersed in the cold Ca-omitted and Mg-omitted Hanks' balanced salt solution (HBSS) (Gibco, Grand Island, N.Y.). The tail artery was digested twice with HBSS enzyme solution II and I consecutively. Each digestion lasted for 1 hour. HBSS enzyme solution I contained CaCl2 (0.2 mM), collagenase/dispase (1.5 mg/ml) (Boehringer Mannheim GmbH, West Germany), elastase (Type I, 0.5 mg/ml) (Sigma Chemical Co., St. Louis, Mo.), trypsin inhibitor (Type I, 1 mg/ml) (Sigma Chemical Co.) and bovine serum albumin (BSA) (fatty acid free, 2 mg/ml) (Sigma Chemical Co.). HBSS enzyme solution II contained collagenase (Type II, 1 mg/ml) (Sigma Chemical Co.), trypsin inhibitor (0.3 mg/ml) and BSA (2 mg/ml). The cell suspension were then seeded into 96 flat-bottom well tissue culture plates in DMEM medium with 10% FCS and incubated at 37° C. in a humidified atmosphere with 5% CO2 in air for 36 hours to allow cells attachment to the bottom of the plate. The medium was changed to DMEM with 0.4% of FCS to render the cells quiescent for 2-4 days. This procedure synchronised cells in the Go-G1 boundary. PHF and shark cartilage were dissolved in DMEM with 10% FCS. PHF alone or PHF plus shark cartilage was added into the quiescent cells. After incubation for 36 hours, the cells were pulsed with 3H-thymidine (0.2 (/well and incubated for another 24 hours. The medium was then removed and the cells were washed twice with HBSS followed by a 15-30 minutes incubation with 0.1% of trypsin at room temperature. The cells were then harvested onto filter paper by the cell harvest. The amount of radioactivity incorporated into cells was determined using a liquid scintillation counter. As shown in FIG. 4, PHF stimulated VSMC cell proliferation in WKY rats. FIG. 5 shows that the stimulating effect of PHF on VSMC in WKY rats can be inhibited by shark cartilage extract. FIG. 6 shows that shark cartilage inhibited VSMC proliferation of SHR rats.

EXAMPLE 6

Chemical Composition of Shark Cartilage Extract (1). Determination of Protein Content Total protein content is determined using the BCA method. The BCA Protein Assay Reagent is purchased from the PIRRCE. A standard curve of protein standards of known concentration can be constructed by using the BSA (bovine serum albumin) standard solution provided with the BCA Protein Assay Reagent Kit. Twenty-four glass tubes were set in three rows and seven columns for standard samples and another four tubes were set for spectrophotometer calibration. Ninety-five, 90, 80, 70, 60, 50, 40, and 30 μl of 0.9% sodium chloride was applied into the first row of the tubes respectively. The same procedure was repeated for the second and third rows. Five, 10, 20, 30, 40, 50, 60, and 70 μl of standard protein (provided with the kit and at a concentration of 2 mg/ml) were applied into the first row of tubes containing 0.9% sodium chloride. The same procedure was repeated for the second and third rows. Two mls of the Working Reagent, which is a mixture of 50 parts of Reagent A and 1 part of Reagent B was then added to each tube. All samples were well mixed and incubated at 37° C. for 30 min. Protein was determined by measuring the absorbency at 562 nm with a spectrophotometer (Model PU 8620 UV/VIS/NIR, Philips). The mean values of each concentration of standards were calculated and a standard curve was constructed by using the Analysis of the Regression Line No. 5, Pharmcologic Calculation System-Version 4.2A. This standard curve was used to determine the protein concentration for each unknown sample. 1% of shark cartilage extract solution was prepared in double distilled (DD) water. The protein concentration (mg/ml) of the sample solution was calculated by using the standard curve and shark cartilage protein content by percentage was calculated by using the following formulation:

Protein %(w/w)=sample protein concentration (mg/ml)× dilution factor (2.5)/sample concentration (10 mg/ml)×100.

To obtain accurate data for the standard curve and shark cartilage sample, the procedure for standard curve construction and shark cartilage extract protein content determination were carried out simultaneously, the Working Reagent was the last reagent added into all tubes for the standard protein samples and the shark cartilage sample.

The protein content is 15.11(2.79(%) in a total of 16 batches of shark cartilage extract.

(2). Determination of Mucopolysacchrides

The method was adapted from P. Whiteman (Biochem. J. 131:351-357, 1973) and E. Gold (Analytical Biochemistry 99: 183-188, 1979). Standard sample Chondroitin Sulfate C was purchased from Sigma chemical Co., Cat No. C-4384, Lot No. 21H0103. Standard or samples were prepared by dissolving 10 mg Chondroitin Sulfate C or shark cartilage extract in 50 ml DD water. Reaction reagent was prepared by dissolving 20 mg Aleian Blue 8GX in 20 ml buffer (5.07 g magnesium chloride and 3.4 g sodium acetate in 500 ml water) and 0.2 ml acetic acid. A series of shark cartilage extract samples ranging 40-200 μg in 1 ml was added into a 50 ml-plastic tube respectively. One ml of reaction reagent was added into these tubes. The mixture was equilibrated for 2 hours at room temperature with stirring. Twenty ml of 95% ethanol was added followed by centrifugation. After decanting the supernatant, three ml of 0.2M calcium chloride was added to the precipitate. The mucopolysaccharide content was determined by measuring the absorbency of the calcium chloride solution of precipitate at 620 nm.

The mucopolysaccharide content was 50.33(2.25(%) in 6 batches of shark cartilage extract.

(3). Isolation and Determination of Chondroitin C

The method was adapted from L. Roden, et al., Methods in Enzymology (1972), Vol. 28, Complex Carbohydrates part B, ed. by V. Ginsburg. Amberlite IR-120 Plus was purchased from Sigma Chemical Co., Cat No. IR-120 Plus. Calcium acetate buffer was prepared by adding 1.2L DD water to 62.5 g calcium acetate. pH was adjusted to 4.5 with 35.5 ml glacial acetic acid. Two grams of shark cartilage extract was added to 400 ml of calcium acetate buffer in a 2L-glass flask. Sample solution was heated in a water bath at 37° C. for 20 min, then cooled to room temperature. Ethanol (100%, 116.25 ml) was added to the sample solution very slowly with vigorous stirring at room temperature. Set the flask at 4° C. bath for 3 hours followed by centrifugation (11,000 rpm, 19,000 g) for 15 min at 4° C. The precipitate was dissolved in DD water and freeze dried. The supernatant was warmed to room temperature and was added into 80 ml of ethanol (100%) slowly with vigorous stirring. The flask was set in 4° C. bath again overnight with slow stirring. The solution was centrifuged at 4° C. (11,000 rpm) for 15 min. The second precipitate was dissolved in DD water and freeze dried, The supernatant was warmed to room temperature and 100 ml ethanol was added slowly with vigorous stirring. Again the flask was set in 4° C. bath overnight with slow stirring followed by centrifugation at 11,000 rpm for 15 min. DD water (125 ml) was added to the third precipitate which was applied to an Amberlite IR-120+(Na+ form) column (2.5×16 cm, about 60 g of Amberlite IR-120 Plus). The column was washed with 75 ml of DD water. After adding 1.168 g NaCl to make the solution 0.1M in salt 3 volumes (600 ml) of absolute ethanol was applied with vigorous stirring. Again, the flask was placed in 4–° C. bath overnight followed by centrifugation (11,000 rpm) at 4° C. for 15 min. The last precipitate was dissolved in DD water and freezes dried. The weight of last precipitate represents the amount of chondroitin sulfate C.

The chondroitin sulfate C content was 5.9(1.98(%) in 2 batches of shark cartilage extract.

BRIEF DESCRIPTION OF THE DRAWINGS

As shown in FIG. 1, the shark cartilage extract produced no effect in SD rats but decreased the blood pressure in SHR rats.

As shown in FIG. 2, the shark cartilage extract produced a decrease in blood pressure in all of the rats.

Figure 1:
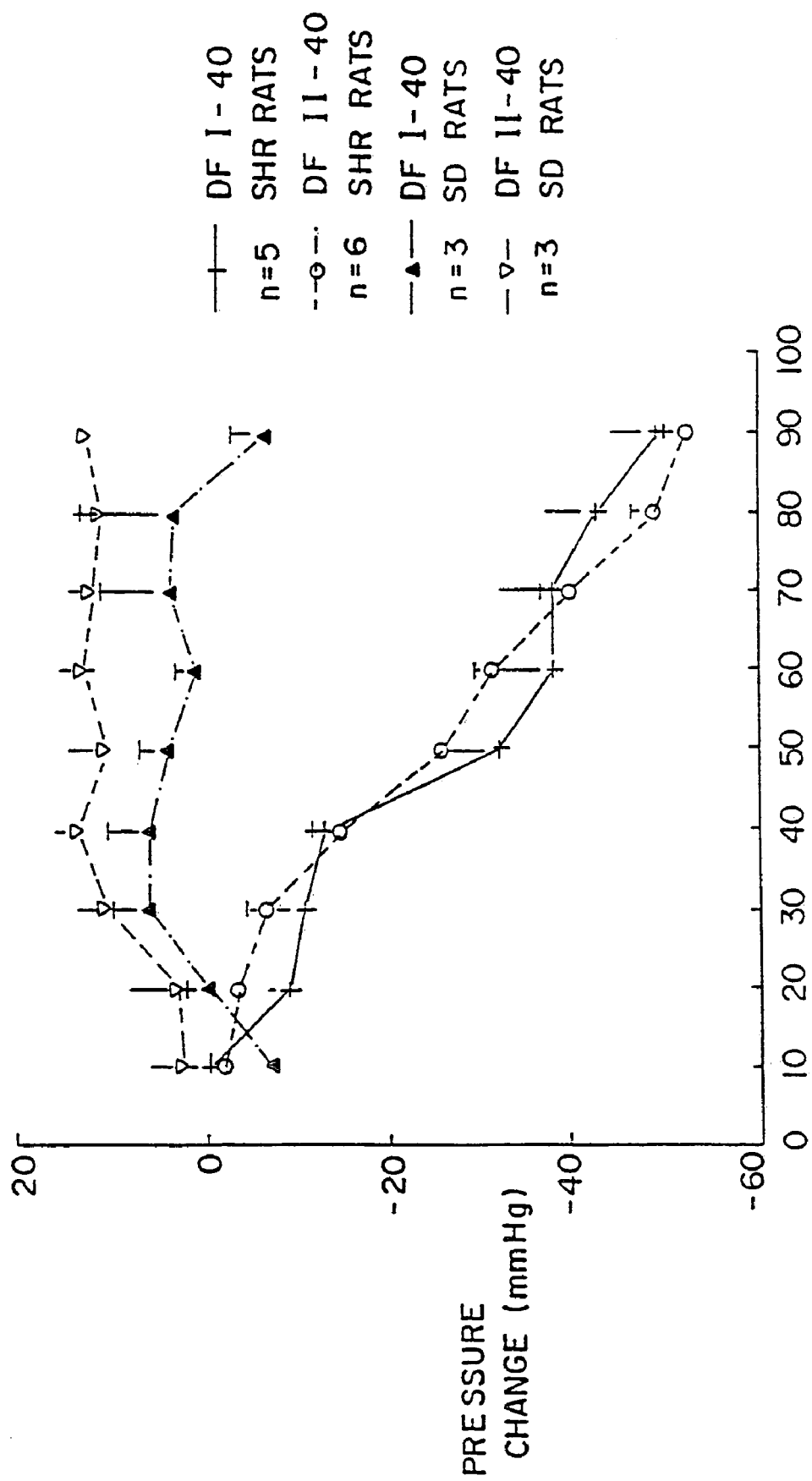
FIG. 1 shows the results of an IV bolus injection of shark cartilage extract in SHR and SD rats.
Figure 2:
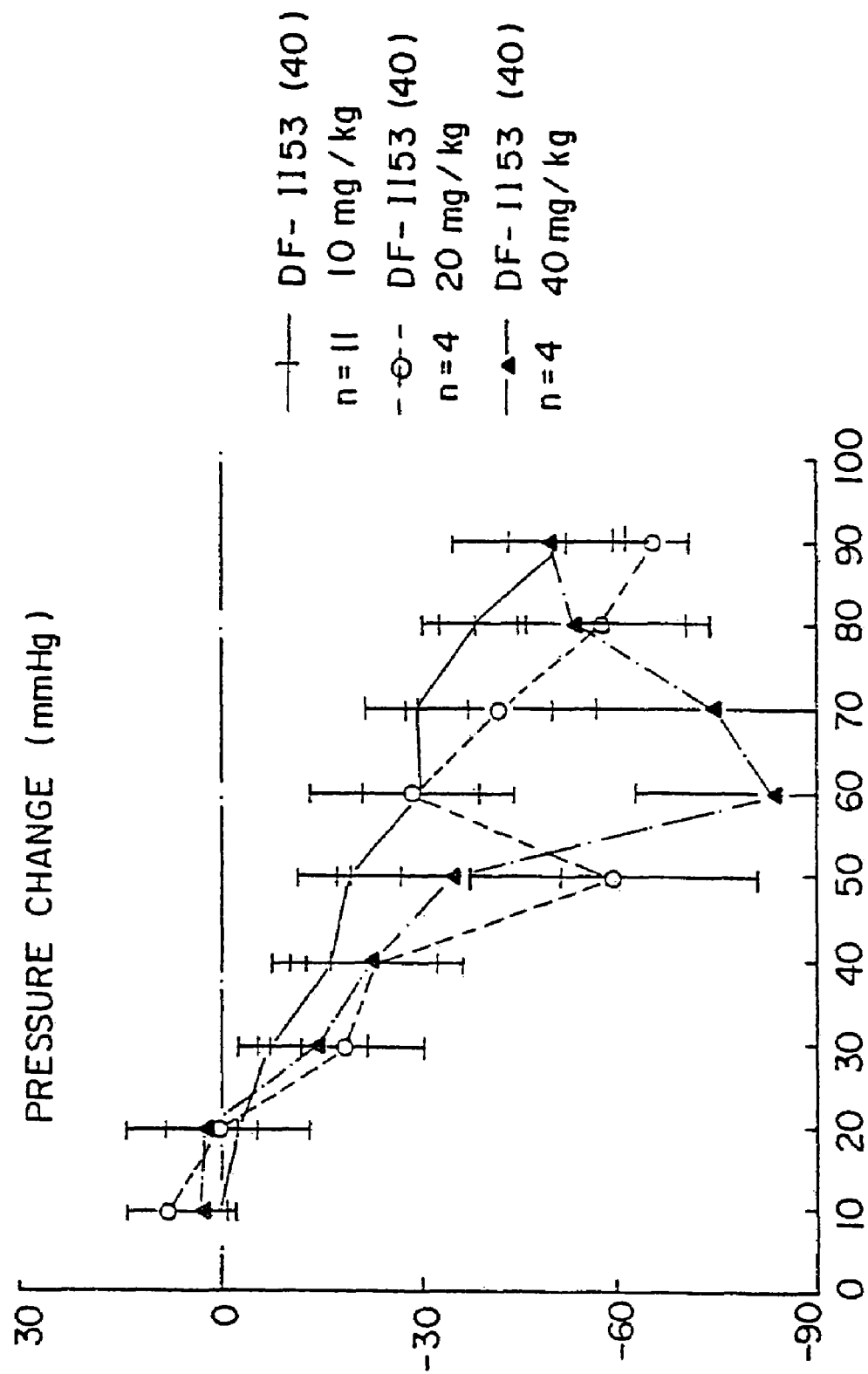
FIG. 2 shows the results of gavage administration of shark cartilage extract in SHR rats.
Figure 2A:
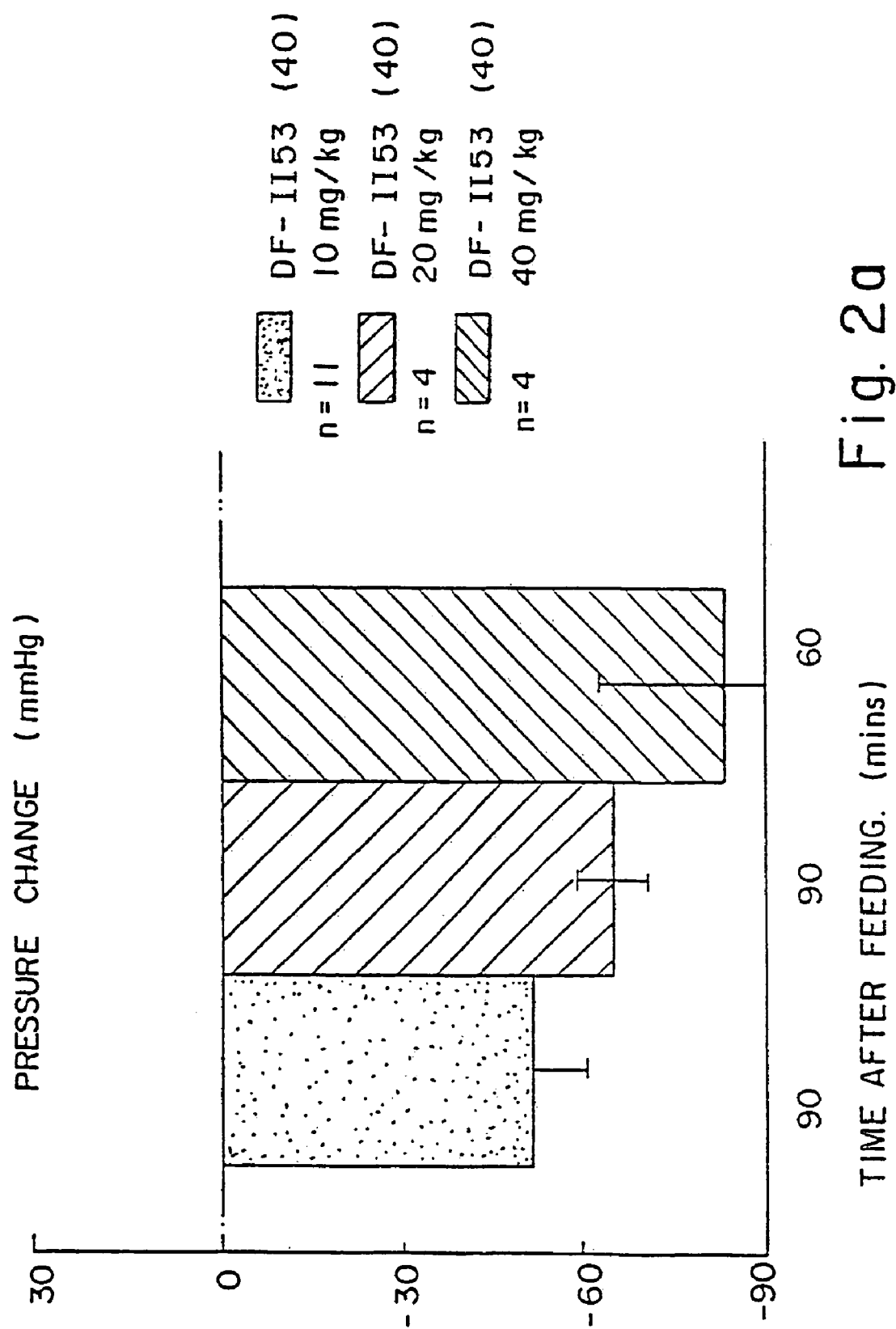
FIGS. 2a and 2b show that the decrease in blood pressure is dose related and the maximum decrease is reached at around 50-60 minutes.
Figure 2B:
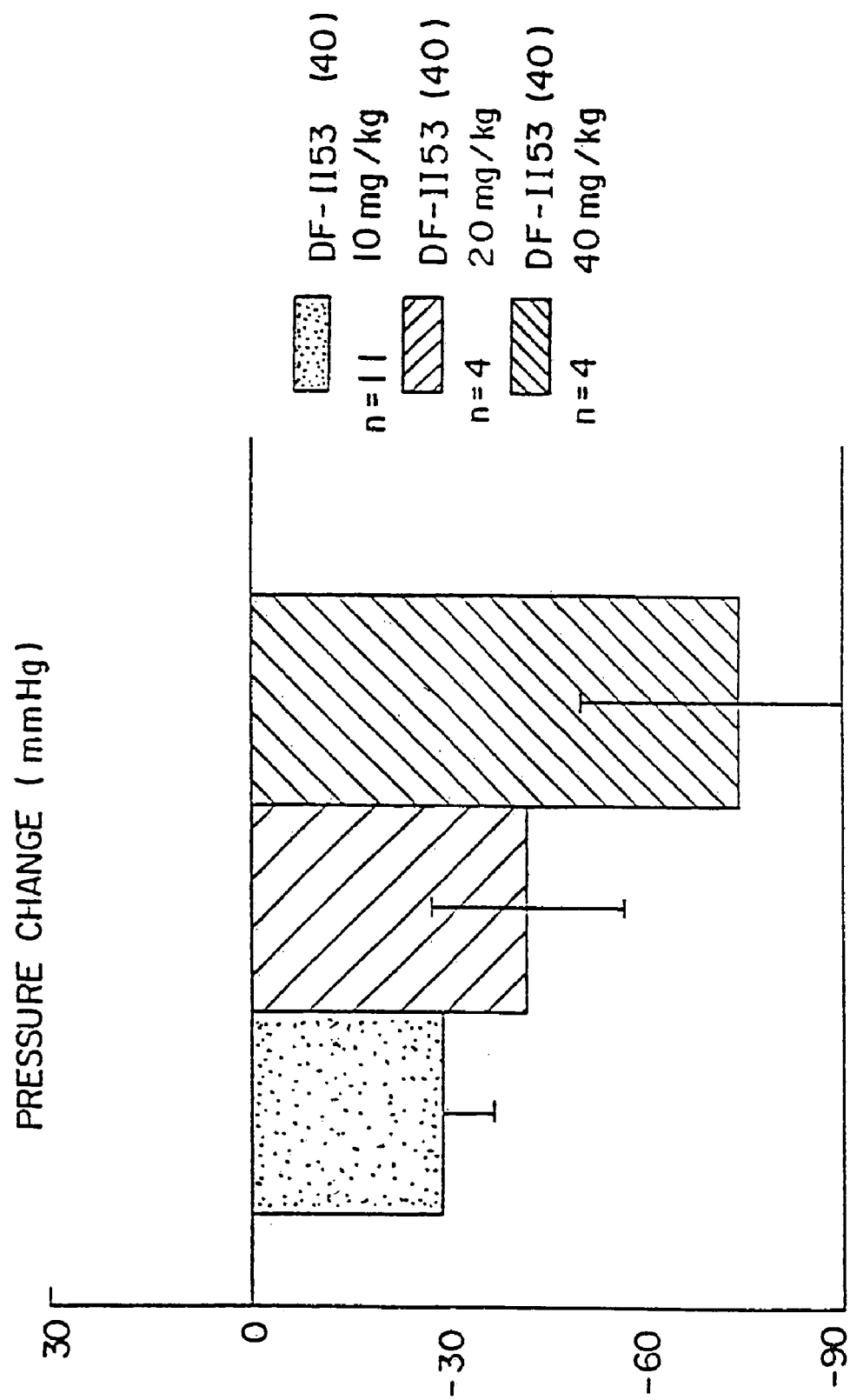
Figure 3:
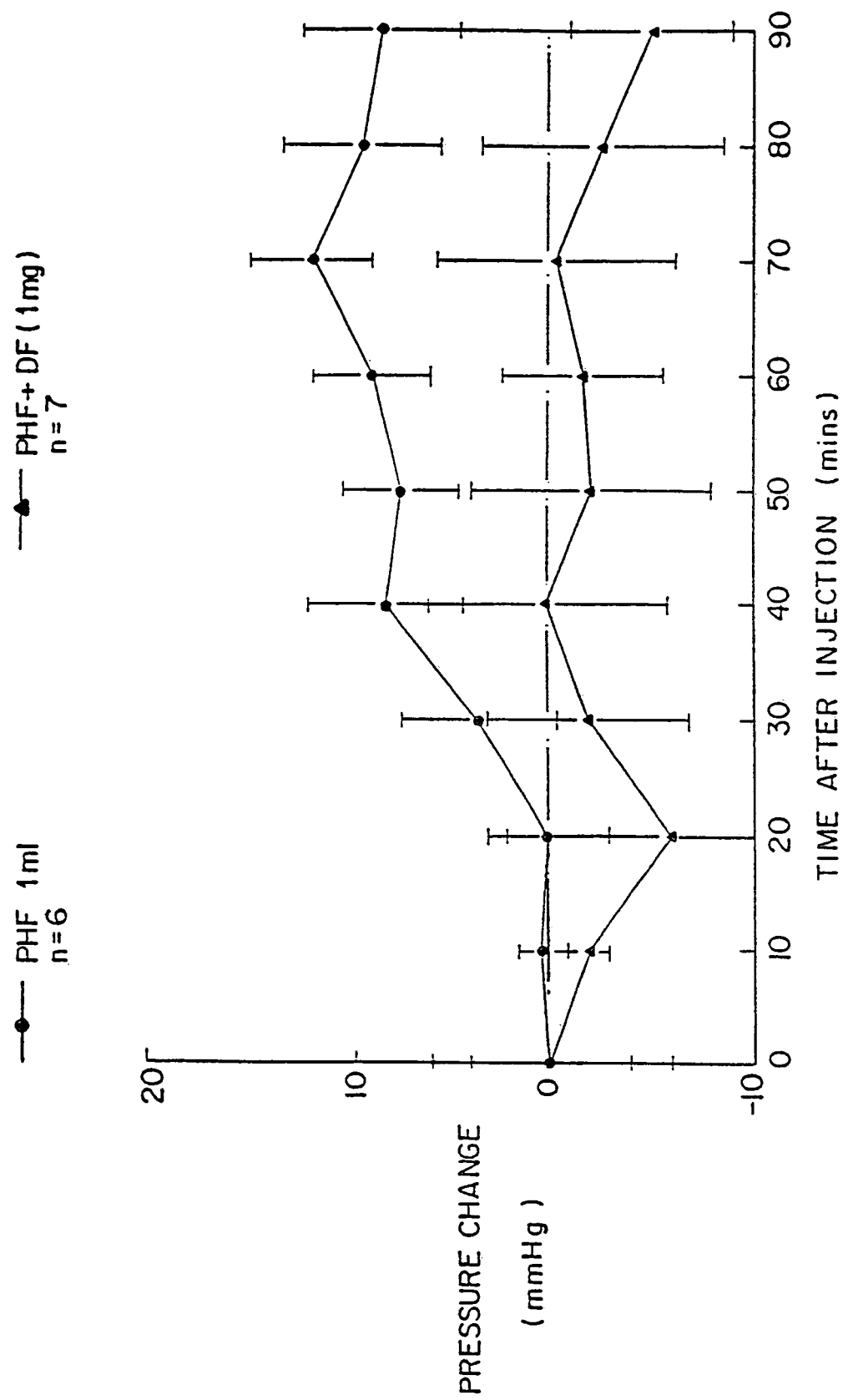
FIG. 3 shows that PHF produces a delayed increase in blood pressure and the shark cartilage extract counteracts this response.
Figure 4:
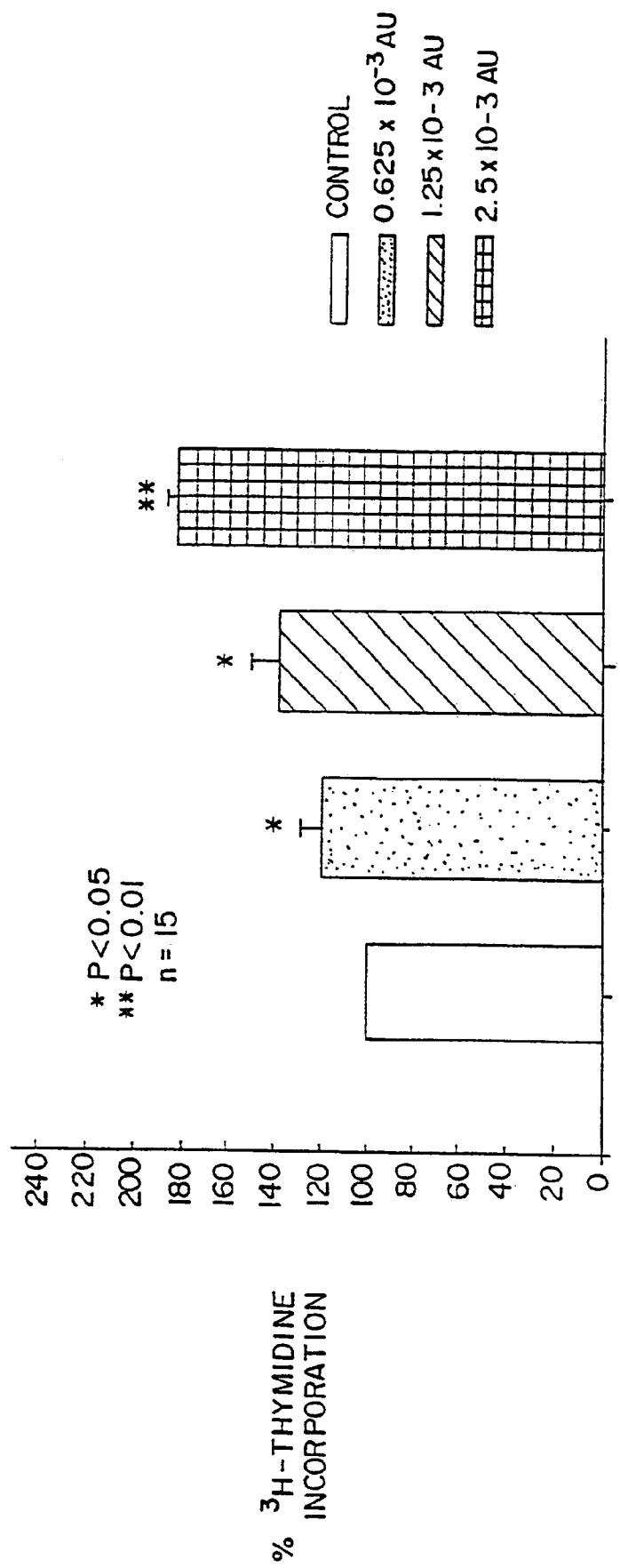
FIG. 4 demonstrates that PHF stimulated VSMC of WKY rats proliferation in a dose-dependent manner. At the doses of 0.625×10-3, 1.25×10-3 and 2.5×10-3 absorption unit, PHF increased cell proliferation by 120(8.5(%) ($P<0.05$, n=16), 137.91(12(%)($P<0.01$, n=16) and 181.9(14.3(%) ($P<0.05$, n=16) respectively.
Figure 5:
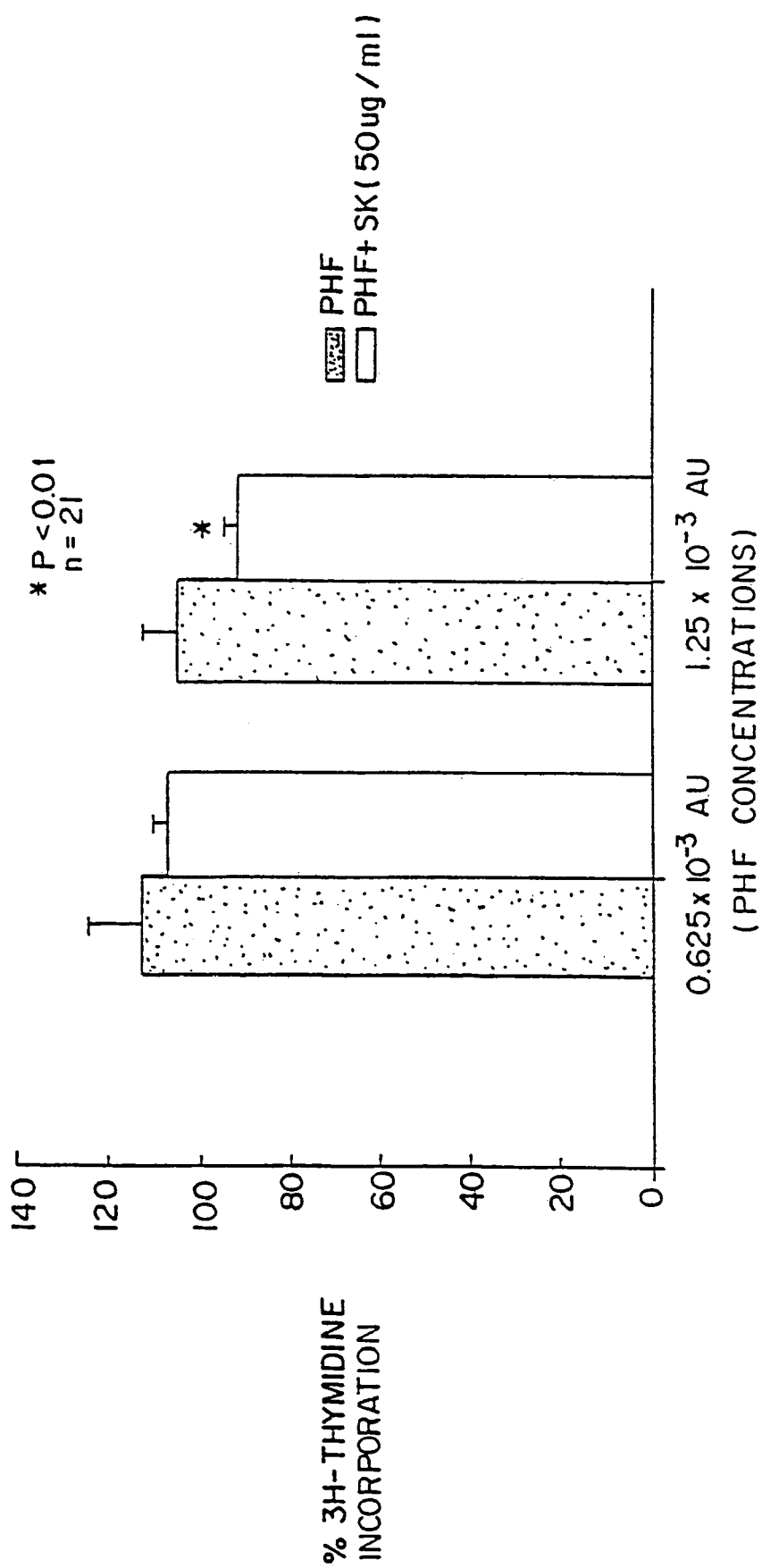
FIG. 5 shows the effect of PHF on VSMC of WKY rats proliferation in the presence of shark cartilage extract. At dose of 50 (g/ml, shark cartilage extract significantly inhibits VSMC proliferation induced by PHF.
Figure 6:
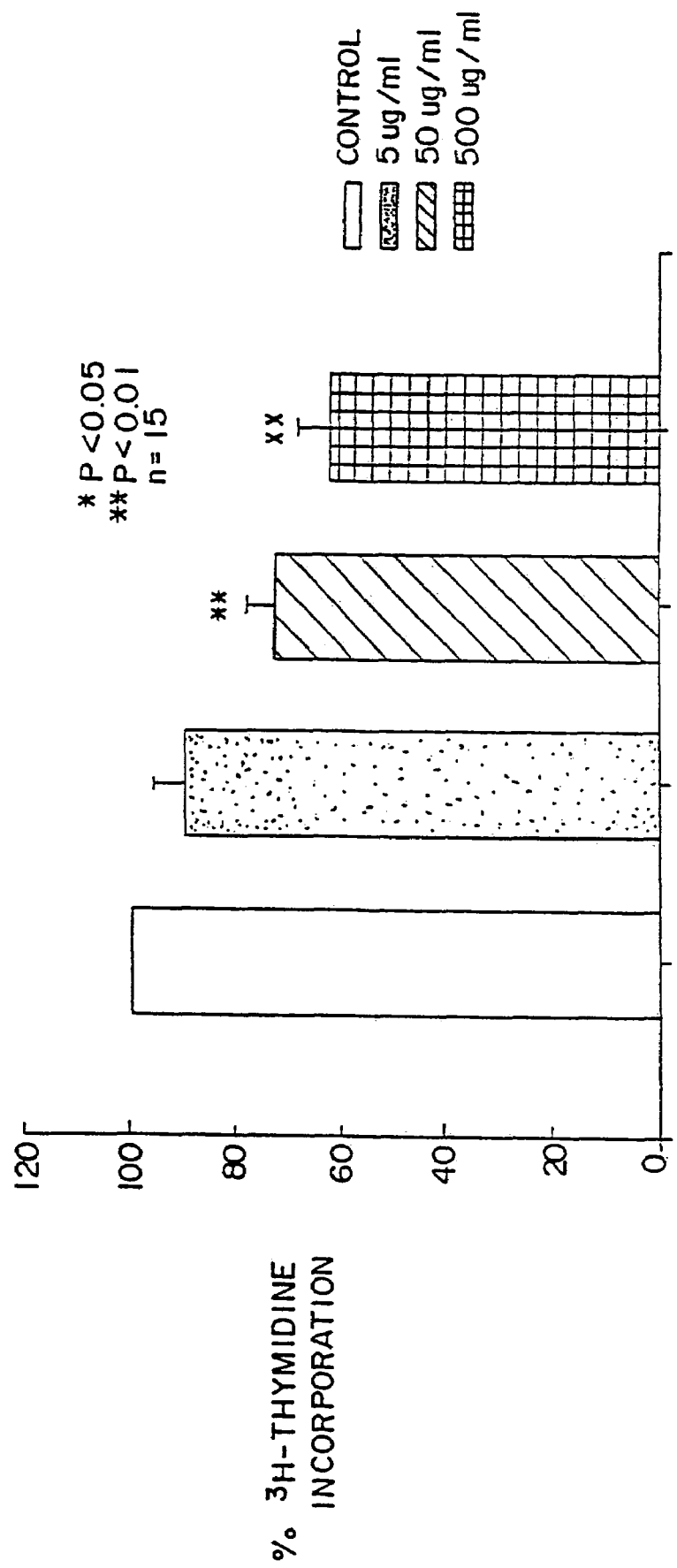
FIG. 6 shows the effects of shark cartilage extract on VSMC of SHR rats. At the doses of 5, 50 and 500 (g/ml, shark cartilage extract inhibits VSMC proliferation in a dose-dependent manner.

The invention claimed is:

1. A method for producing a purified shark cartilage extract with anti-parathyroid hypertensive factor activity, comprising the steps of:

extracting cleaned, dried, ground shark cartilage with $H_2O$ at a temperature between 95-120° C. for 2-4 hours, cooling the resulting suspension to between 40-60° C., centrifuging the cooled suspension at between 5200-5700 rpm to separate the suspension into supernatant 1 and pellet, holding the supernatant 1 in a cooling tank at 4-8° C., extracting the pellet a second time with $H_2O$ at a temperature between 85-120° C. for 2-4 hours, cooling the resulting suspension to between 40-60° C., centrifuging the cooled suspension at between 5200 to 5700 rpm to separate the suspension into supernatant 2 and pellet, pooling supernatant 1 with supernatant 2, and spray drying the pooled supernatants to obtain the shark cartilage extract.

2. The method according to claim 1, wherein said extracting steps are conducted at 95° C. for 2 hours.

3. The method according to claim 1, wherein a decanter centrifuge is used in said centrifuging steps.

4. The method according to claim 1, further comprising concentrating the pooled supernatants until a solids content of between 8-10% is reached.

* * * * *